United States Patent [19]

Yoshida et al.

[11] Patent Number: Plant 6,519

[45] Date of Patent: Jan. 10, 1989

[54] APPLE TREE 'SANSA'

[75] Inventors: Yoshio Yoshida, Ibaraki; Tadayuki Haniuda, Suzaka; Shichiro Tsuchiya, Morioka; Tetsuro Sanada, Ibaraki; Tetsuo Masuda; Hideo Bessho, both of Morioka, all of Japan; Donald W. McKenzie, Havelock North, New Zealand

[73] Assignee: Fruit Tree Research Station, Ministry of Agriculture Forestry and Fisheries, Tsukuba, Japan

[21] Appl. No.: 25,029

[22] Filed: Mar. 12, 1987

[30] Foreign Application Priority Data

Sep. 2, 1986 [JP] Japan ..... 61-2023

[51] Int. Cl.[4] ..... A01H 5/00

[52] U.S. Cl. ..... Plt./34

[58] Field of Search ..... Plt./34

[56] References Cited

PUBLICATIONS

Official Gazette No. 17915 (Oct. 31, 1986), p. 11.

*Primary Examiner*—James R. Feyrer

*Attorney, Agent, or Firm*—Armstrong, Nikaido, Marmelstein & Kubovcik

[57] ABSTRACT

Disclosed herein is an apple tree of an early-maturing cultivar which is reciprocal-fertile with main cultivars and has a high productivity with a regular crop and almost no physiological fruit drop. The tree has leaves with yellow mottle inherited from the male parent 'Akane', and can produce a fruit suitable for dessert and with a good keeping quality. The fruit has a skin of a yellowish green ground color with bright red, and a fine, juicy and crisp flesh which has a whitish yellow color, a good texture, a moderate sweetness and moderate acidity, giving a good sweet-acid balance and an excellent dessert quality.

7 Drawing Sheets

BACKGROUND OF THE VARIETY

The present invention relates to a new and distinct variety of apple tree having fruit which matures early in the season, is reciprocal-fertile with main cultivars, and has a high productivity with a regular crop and almost no physiological fruit drop. The tree has leaves with yellow mottle inherited from 'Akane' (i.e., male parent of the new variety of apple tree according to this invention), and can produce a fruit suitable for dessert and with a good keeping quality. The fruit has a skin of a yellowish green ground color with bright red, and a fine, juicy and crisp flesh which has a whitish yellow color, a good texture, a moderate sweetness and moderate acidity, giving a good sweet-acid balance and an excellent dessert quality.

All places and address mentioned in this specification are in Japan, unless otherwise specified.

Our breeding program was aimed at obtaining a new variety of apple tree producing, first, a fruit having a high marketability for dessert use due to a good appearance, taste and keeping quality; second, maturing early in the season with little physiological fruit drop; and third, easy to grow and productive.

The new variety of apple tree according to this invention originated from crossing 'Gala' (♀)×'Akane (♂)', and was named 'Sansa' in October, 1986. Particularly, pollen of 'Akane (♂)' was sent to Dr. D. W. Mckenzie, Department of Scientific and Industrial Research (DSIR) of New Zealand, in May, 1969, and pollinated with 'Gala (♀)' in October, 1969. The seeds resulted from this crossing were returned to the Morioka Branch of the Fruit Tree Research Station, Ministry of Agriculture, Forestry and Fisheries, residing at Nabeyashiki, Simokuriyagawa, Morioka-shi, Iwate-ken, Japan, in April, 1970, and 386 seedlings were raised from the seeds. The 'Sansa' tree was given the number '2279' and top-worked onto the M26/M prunifolia tree in 1974. The tree was selected by continual research, which was started in 1976 and concerned the quality of the fruit and the growing character. From 1981, the thus-selected tree was subjected to local adaptability tests at experimental stations in apple growing districts of Japan, e.g., in Akita-ken, Yamagata-ken and the like, as the number 'Morioka-42'. As a result, this new variety of apple tree according to this invention was judged to have a better quality fruit, when compared with 'Tsugaru' (i.e., main cultivar of Japan, having almost the same ripening time as this new variety of apple tree).

The pedigree of 'Sansa' according to this invention is shown in FIG. 1.

'Gala', used as a female parent in the breeding of 'Sansa', originated from a crossing of 'Kidd's Orange'×'Golden Delicious' by J. H. Kidd in Greytown, Wairarapa, New Zealand, was selected in 1939 and introduced in 1960. The main botanical characteristics of 'Gala' are as follows.

Tree: Precocious.
- *Vigor.*—Strong.
- *Spur.*—Bearing heavily.
- *Productivity.*—Heavy and regular.

Branches: Long and pliant.

Leaves: Healthy with tendency to leaf-burn.

Flowers: Blooming in mid-May in Morioka, Japan.

Fruit:
- *Size.*—Medium, 200 g.
- *Shape.*—Oval, round in transverse outline, uniform.
- *Cavity.*—Wide and deep with slender and very long stalk.
- *Basin.*—Medium width and depth.
- *Color of skin.*—Pale yellow to golden yellow, heavily striped with a red color.
- *Skin.*—Glossy, thin, not bruising readily, completely free from blemish, and no russet.
- *Color of flesh.*—Yellow.

*Flesh.*—Fine, firm, crisp and very juicy.

*Taste.*—Very sweet.

*Maturity.*—Ripening at almost the same time as 'Red Gold', and two weeks earlier than 'Jonathan' and 'Starking Delicious', e.g., late September to early October in Morioka, Japan.

*Keeping quality.*—Better storage quality and longer shelf-life after removal from storage than 'Cox's Orange Pippin'.

Resistance to pests and diseases: Susceptible to apple mosaic, but resistant to Alternalia blotch (*Alternaria mali* Roberts)

Physiological disorder: No problems with various disorders, e.g., Bitter pit, Cork spot, Jonathan spot and the like.

'Akane', used as a male parent in the breeding of 'Sansa', originated from a crossing of 'Jonathan'×-'Worcester Pearmain' on May 17, 1939 at the Tōhoku Branch of the Horticultural Research Station, of the Ministry of Agriculture and Forestry, residing at Fujisaki-machi, Aomori-ken, Japan, was selected from among the seedlings, and thereafter, was subjected to local adaptability tests at many experimental stations in apple growing districts of Japan, as 'Nu-50'. As a result, the tree was judged to be promising, and was named 'Akane' in October, 1970. The main botanical characteristics of 'Akane' are as follows.

Tree:

*Shape.*—Slightly upright, semi-dwarf.

*Vigor.*—Weak.

*Axillary flower bud.*—Few to very few.

*Production.*—Not highly productive, tendency toward biennial bearing.

Leaves: Yellow mottle leaves, which are considered to be hereditary characteristic and not virus originating.

*Shape.*—Roundish oval.

Flowers: Reciprocal-fertile with main cultivars, e.g., 'Red God', 'Starking Delicious' and the like.

*Flowering time.*—Blooming with 'McIntosh', e.g., in mid-May in Morioka, Japan.

*Physiological fruit drop.*—Some June and pre-harvest dropping.

Fruit:

*Size.*—Medium, average weight 180–200 g.

*Shape.*—Round oblate to oblate.

*Cavity.*—Wide and medium to deep in depth.

*Basin.*—Medium in width and medium to slightly deep in depth.

*Color of skin.*—Attractive solid bright red similar to that of 'Jonathan'.

*Skin.*—Thick, tough, smooth, with abundant, small and clear lenticels and slight to moderate amount of russet, and covered with slight scarfskin.

*Color of flesh.*—White.

*Flesh.*—Firm, a little coarse, juicy, and crisp.

*Taste.*—Sub-sweet (about 10 in refractometer index), sub-acid, most resembling 'Jonathan' in flavor, and having an excellent quality for dessert and canning.

*Maturity.*—Maturing in early-to-mid September in Morioka, Japan.

*Keeping quality.*—Can be kept for 3 to 4 weeks.

Resistance to pests and diseases . . . Fairly resistant to Alternaria blotch and Apple fruit spot (*Mycosphaerella pomi* (Pass.) Lindau).

We asexually reproduced this new and distinct variety of apple tree 'Sansa', by ordinary grafting or budding at the Morioka Branch of the Fruit Tree Research Station, Ministry of Agriculture, Forestry and Fisheries, residing at Morioka-shi, Iwate-ken, Japan, and confirmed the homogeneity and stability of 'Sansa' according to this invention.

An application for this new variety of apple tree 'Sansa' under the Seeds and Seedlings Law of Japan was filed on Sept. 2, 1986.

SUMMARY OF THE VARIETY

This new variety of apple tree has a slightly weak vigor, but has a good spur-bearing habit and a quite strong resistance to Alternaria blotch and Scab, is reciprocal-fertile with main cultivars and productive with a regular crop and almost no physiological fruit drop, and has leaves with genetic yellow mottle inherited from the male parent 'Akane'. The tree produces a rather small fruit maturing early in the season, and having a two to three weeks keeping quality which is good as an early-maturing cultivar, a conical shape, a yellowish green ground-colored skin with a bright red coloring superior to 'Tsugaru', and a fine, juicy and crisp flesh which has a whitish yellow color, a good texture, a moderate sweetness and moderate acidity, and gives a good sweet-acid balance and an excellent dessert quality superior to 'Tsugaru'.

DESCRIPTION OF THE VARIETY

The botanical characteristics of the new and distinct variety of apple tree 'Sansa' are as follows:

Tree: Moderate precocious.

Figure 2:
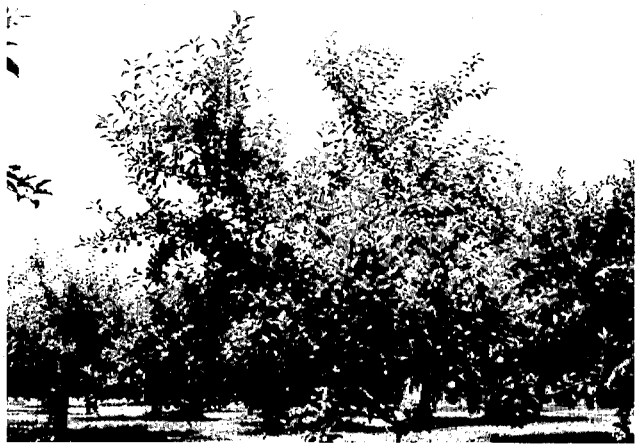
FIG. 2 is a photograph of a shape of the new variety of apple tree.

*Shape.*—Slightly upright (See FIG. 2).

*Vigor.*—Slightly weak.

*Spur.*—Bearing very well.

*Axillary flower bud.*—Few to very few.

*Bud breaking time.*—Mid-April in Morioka, Japan.

*Production.*—Heavy with regular crop.

Leaves: Having genetic yellow mottle inherited from 'Akane', the degree of yellow mottle being lighter than 'Akane'.

*Shape.*—Round to oblong.

*Color.*—Green.

Figure 3:
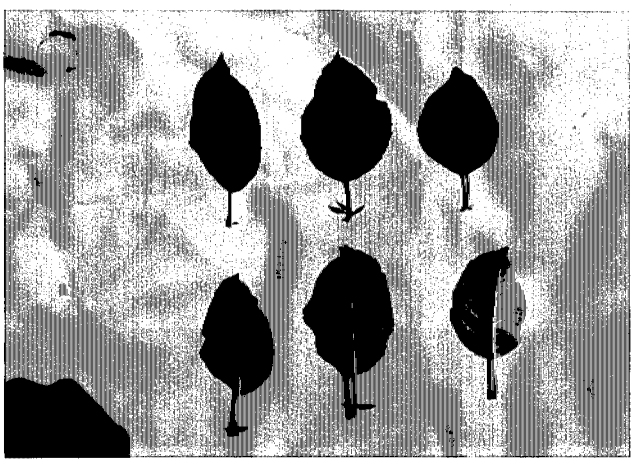
FIG. 3 is a photograph of leaves of the new variety of apple tree, comparing with those of 'Gala' (left) and 'Akane' (right)

*Length of petiole.*—Long. (See FIG. 3).

Flowers: Reciprocal-fertile with main cultivars (e.g., 'Jonathan', 'Starking Delicious', 'Tsugaru', and 'Fuji'), and self-sterile.

Figure 4:
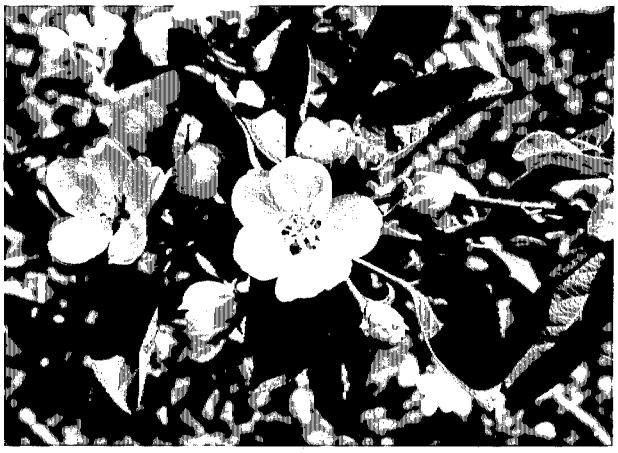
FIG. 4 is a photograph of the new variety of apple tree in blooming condition.
Figure 5:
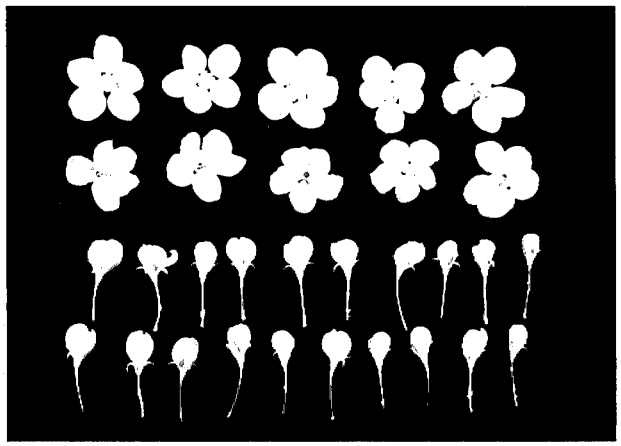
FIG. 5 is a photograph of flowers in opened and unopened stages of the new variety of apple tree.
Figure 6:
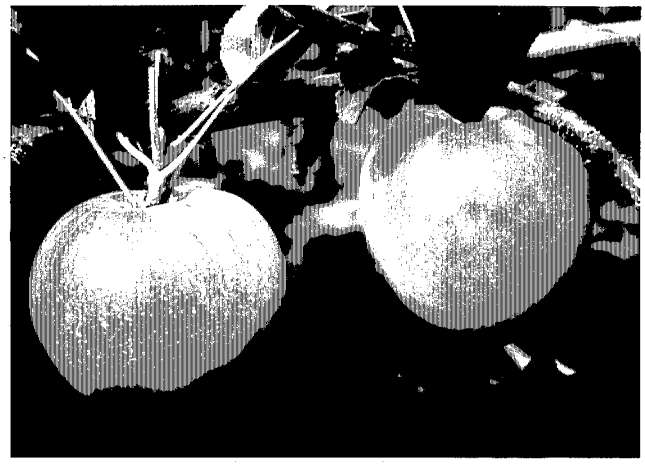
FIG. 6 is a photograph of the new variety of apple tree in bearing condition.

*Size.*—Medium (See FIGS. 4 and 5).

*Color.*—White, but pale pink in an unopened stage (See FIG. 5).

*Pollen.*—Abundant.

*Flowering time.*—Blooming at the same season as 'Gala' and 'Tsugaru', and in mid-May in Morioka, Japan.

*Physiological fruit drop.*—Almost no June and preharvest dropping, quite different from 'Tsugaru'.

Fruit: (see FIGS. 7 to 12)

*Size.*—Rather small, average weight 200–250 g.

*Shape.*—Conical, and not as plump as 'Tsugaru'.

Figure 7:
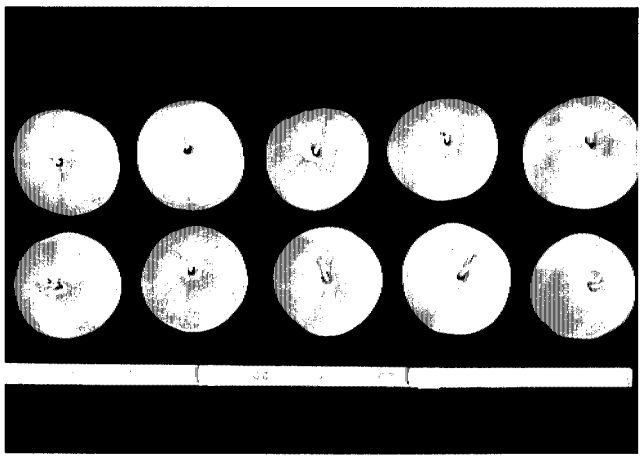
FIG. 7 is a photograph of cavities of fruit of the new variety of apple tree.
Figure 8:
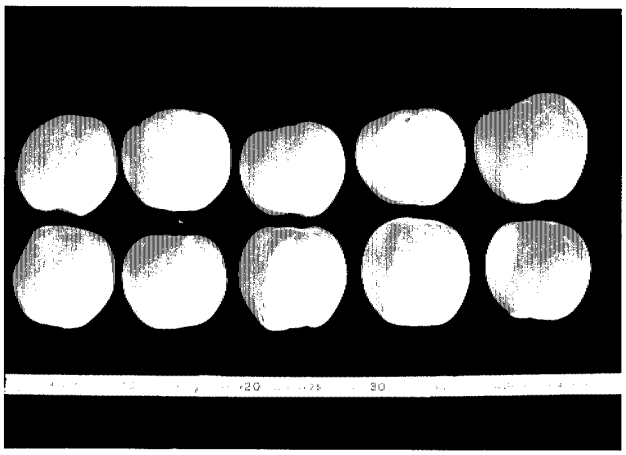
FIG. 8 is a photograph giving side views of fruit of the new variety of apple tree.

*Cavity.*—Medium width and depth with stalk of medium length (2.5 cm) and thickness (See FIG. 7).

Figure 9:
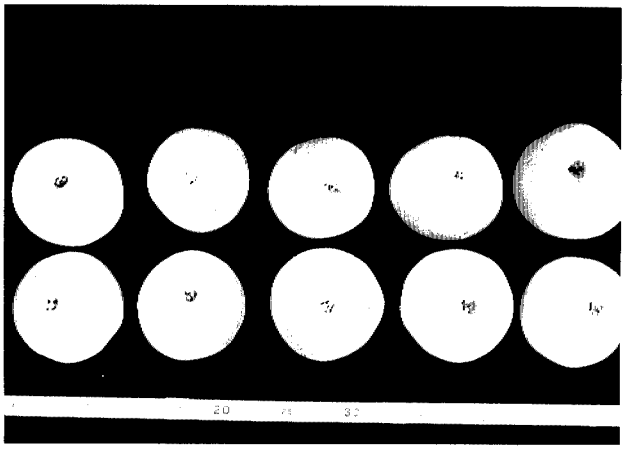
FIG. 9 is a photograph of basins of fruit of the new variety of apple tree.
Figure 10:
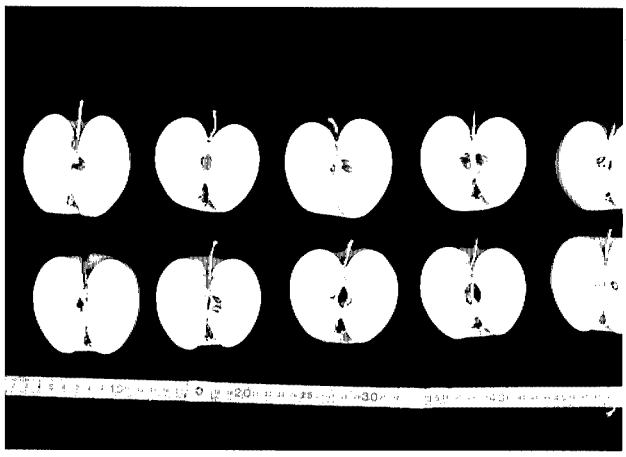
FIG. 10 is a photograph of longitudinal-sectional views of fruit of the new variety of apple tree.
Figure 11:
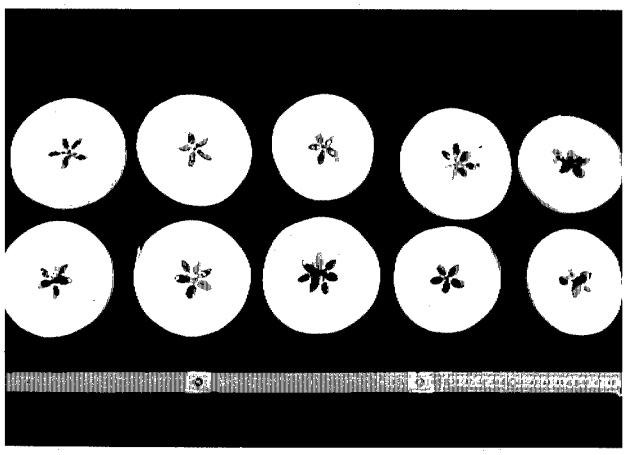
FIG. 11 is a photograph of cross-sectional views of fruit of the new variety of apple tree; and, FIG. 12 is a photograph of side, longitudinal-sectional and bottom (basin) views of fruit, from the left, of the new variety of apple tree.
Figure 12:
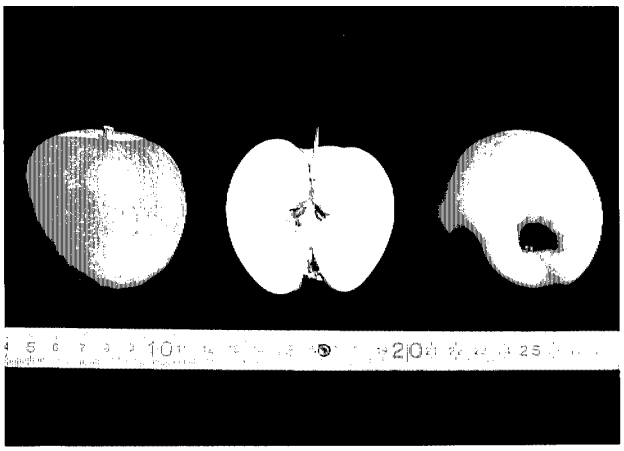

*Basin.*—Medium width and depth (See FIG. 9).

*Color of skin.*—Yellowish green ground color with a bright red coloring better than 'Tsugaru', with stripe.

*Skin.*—Moderate in surface texture, medium shininess, with scarfskin and small lenticels, and having a tendency to have a small to medium amount of russet around the basin.

*Color of flesh.*—Whitish yellow.

*Flesh.*—Fine, juicy and crisp, with a good texture, a medium firmness (14 lbs.), a weak flesh-browning, and none or a little water core.

*Taste.*—Moderate sweetness (about 13 in refractometer index, which is high as an early-maturing cultivar and a little higher than that of 'Tsugaru'), moderate acidity (0.4–0.5% maleic acid content, which weakens the acidity of 'Akane'), no astringency and a little aromatic flavor, which give a good sweet-acid balance and an excellent dessert quality better than 'Tsugaru'.

*Maturity.*—Maturing early in the season, for example, in mid-August in Nagano, Japan, and in early September in the main apple growing districts of the northern part of Japan, e.g., Morioka, Japan. This is about 20 days earlier than 'Gala', 5 to 7 days earlier than 'Tsugaru', and about one week later than 'Akane'.

*Keeping quality.*—Can be kept for two to three weeks on the shelf and for one month in cold storage, with the flesh softening later than 'Tsugaru'. This quality is good for an early-maturing cultivar.

Resistance to pests and diseases: Quite strongly resistant to Alternaria blotch and Scab, moderately resistant to Powdery mildew, rough bark disorder and Apple woolly aphid, and almost no occurrence of Heart rot (Core rot).

Culture: It is necessary to pay attention to the selection of agricultural chemicals and the time of spraying after petal fall, as the skin of fruit tends to have a small to medium amount of russet around the basin. It is preferable to leave the central fruit of a cluster at the time of fruit thinning, because the russet tends to occur in the lateral fruit. Careful attention must be paid to training and pruning, because if the sunlight is insufficient, the coloring of the fruit becomes poor. It is important to ensure the maintenance of yield in such a way that the rather strong vigor of rootstock is used and the trees are densely planted. This is because the 'Sansa' tree has leaves with genetic yellow mottle and a slight weak vigor. This new variety of apple tree is promising as an early-maturing cultivar.

The tree of this new variety 'Sansa' is presently planted and maintained at a field of the Morioka Branch of the Fruit Tree Research Station, Ministry of Agriculture, Forestry and Fisheries, residing at 92 Nabeyashiki, Simokuriyagawa, Morioka-shi, Iwate-ken, Japan.

We claim:

1. A new and distinct variety of apple tree, substantially as illustrated and described herein, characterized over known apple trees by (A) having a slightly weak vigor, but (B) having a good spur-bearing habit and a quite strong resistance to Alternaria blotch and Scab, (C) being reciprocal-fertile with main cultivars and productive with a regular crop and almost no physiological fruit drop, (D) having leaves with genetic yellow mottle inherited from a male parent 'Akane', and (E) producing a rather small fruit (a) maturing early in the season, and (b) having a two to three weeks keeping quality which is good as an early-maturing cultivar, a conical shape, a yellowish green ground-colored skin with a bright red coloring superior to 'Tsugaru', and a fine, juicy and crisp flesh which has a whitish yellow color, a good texture, a moderate sweetness and moderate acidity, and gives a good sweet-acid balance and an excellent dessert quality superior to 'Tsugaru'.

* * * * *

Figure 1:
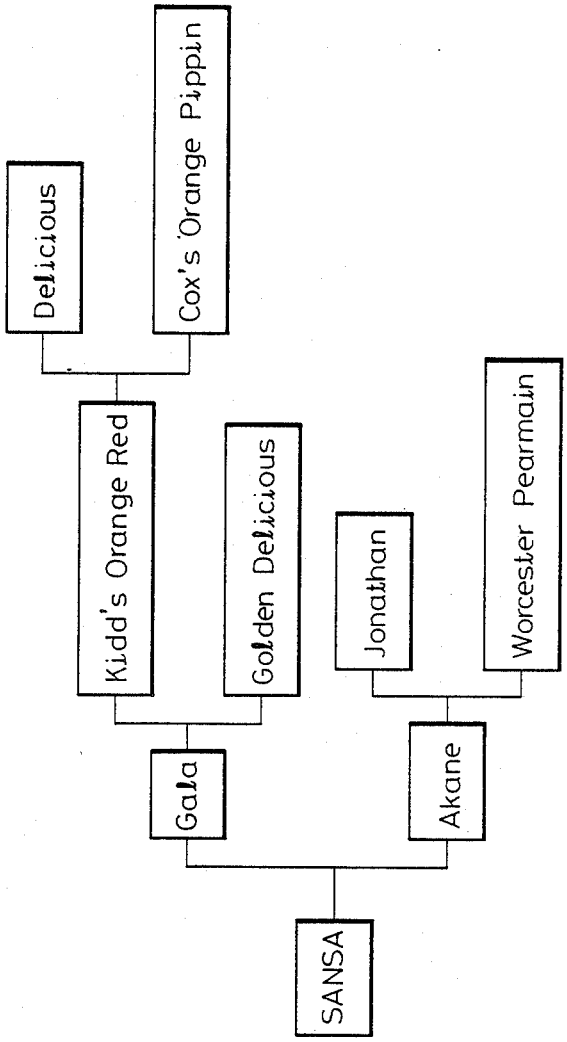
FIG. 1 gives the pedigree of the new and distinct variety of apple tree 'Sansa'.

Fig. 1 Pedigree of 'SANSA'